(12) United States Patent
Allred et al.

(10) Patent No.: US 10,874,495 B2
(45) Date of Patent: Dec. 29, 2020

(54) PACKAGING SYSTEMS INCLUDING SACRIFICIAL COMPOSITION

(71) Applicant: ULTRADENT PRODUCTS, INC., South Jordan, UT (US)

(72) Inventors: Peter M. Allred, Bluffdale, UT (US); Dan E. Fischer, Sandy, UT (US)

(73) Assignee: ULTRADENT PRODUCTS, INC., South Jordan, UT (US)

( * ) Notice: Subject to any disclaimer, the term of this patent is extended or adjusted under 35 U.S.C. 154(b) by 252 days.

(21) Appl. No.: 15/122,333

(22) PCT Filed: Feb. 20, 2015

(86) PCT No.: PCT/US2015/016745
§ 371 (c)(1),
(2) Date: Aug. 29, 2016

(87) PCT Pub. No.: WO2015/142471
PCT Pub. Date: Sep. 24, 2015

(65) Prior Publication Data
US 2016/0367348 A1     Dec. 22, 2016

Related U.S. Application Data

(60) Provisional application No. 61/955,954, filed on Mar. 20, 2014.

(51) Int. Cl.
*A61C 19/02* (2006.01)
*A61K 8/22* (2006.01)
(Continued)

(52) U.S. Cl.
CPC ............ *A61C 19/02* (2013.01); *A61C 19/066* (2013.01); *A61K 8/0204* (2013.01); *A61K 8/22* (2013.01);
(Continued)

(58) Field of Classification Search
CPC ... A61C 19/066; A61C 2202/02; A61C 19/02; A61Q 11/00; A61K 8/22; A61K 2800/52;
(Continued)

(56) References Cited

U.S. PATENT DOCUMENTS

| 5,858,332 A | 1/1999 | Jensen et al. |
| 6,372,816 B1 | 4/2002 | Walz et al. |

(Continued)

FOREIGN PATENT DOCUMENTS

| CN | 1413125 | 4/2003 |
| CN | 1799531 | 7/2006 |

(Continued)

OTHER PUBLICATIONS

International Search Report and Written Opinion for PCT/US15/16745, dated May 20, 2015.
(Continued)

*Primary Examiner* — Anthony D Stashick
*Assistant Examiner* — James M Van Buskirk
(74) *Attorney, Agent, or Firm* — Workman Nydegger

(57) ABSTRACT

Packaging systems are configured for improving long-term stability of a composition. Packaging systems may include a packaging container defining an enclosed volume. The packaging system may additionally include a removable cover that enables the packaging container to be opened and closed such that the packaging container system includes a sealed or sealable volume to contain a main composition in fluid communication with a sacrificial composition. The main composition may include one or more volatile or gas-releasing materials and the sacrificial material may include a stabilizing component that replaces the at least one volatile or gas-releasing component within the main composition or displaces the at least one volatile or gas-releasing component within the enclosed volume. The sacrificial com-
(Continued)

position helps maintain stability of the main composition by accelerating equilibrium of vapors or gases within the headspace of the sealed interior volume.

26 Claims, 6 Drawing Sheets

(51) Int. Cl.
| | |
|---|---|
| A61Q 11/00 | (2006.01) |
| A61C 19/06 | (2006.01) |
| A61K 8/02 | (2006.01) |
| B65D 43/02 | (2006.01) |
| B65D 65/40 | (2006.01) |
| B65D 75/32 | (2006.01) |

(52) U.S. Cl.
CPC .............. *A61Q 11/00* (2013.01); *B65D 43/02* (2013.01); *B65D 65/40* (2013.01); *B65D 75/321* (2013.01); *A61C 2202/02* (2013.01); *A61K 2800/52* (2013.01); *A61K 2800/87* (2013.01)

(58) Field of Classification Search
CPC .............. A61K 2800/87; A61K 8/0204; B65D 75/321; B65D 65/40; B65D 43/02
USPC ............... 206/572, 63.5, 368, 469, 470, 467
See application file for complete search history.

(56) References Cited

U.S. PATENT DOCUMENTS

| | | | | |
|---|---|---|---|---|
| 7,018,622 | B2* | 3/2006 | Goodhart | A61C 19/063 424/401 |
| 7,568,579 | B2* | 8/2009 | Moore | A61C 19/02 206/368 |
| 2001/0000732 | A1* | 5/2001 | Hopkins, Sr. | B65D 43/162 426/106 |
| 2003/0219389 | A1* | 11/2003 | Sagel | A61K 8/0208 424/53 |
| 2007/0114139 | A1 | 5/2007 | Moore | |
| 2009/0214448 | A1* | 8/2009 | Sagel | A61C 19/063 424/53 |
| 2009/0277814 | A1* | 11/2009 | Hamerly | A61F 11/08 206/526 |

FOREIGN PATENT DOCUMENTS

| | | |
|---|---|---|
| EP | 0466068 | 7/1991 |
| EP | 2548816 | 1/2013 |
| JP | 04071560 | 6/1992 |
| WO | 03015656 | 2/2003 |
| WO | 03099247 | 12/2003 |
| WO | 2010010196 | 1/2010 |

OTHER PUBLICATIONS

First Chinese Office Action cited in Chinese Patent Application No. 201580014775.7 dated Nov. 17, 2017.

* cited by examiner

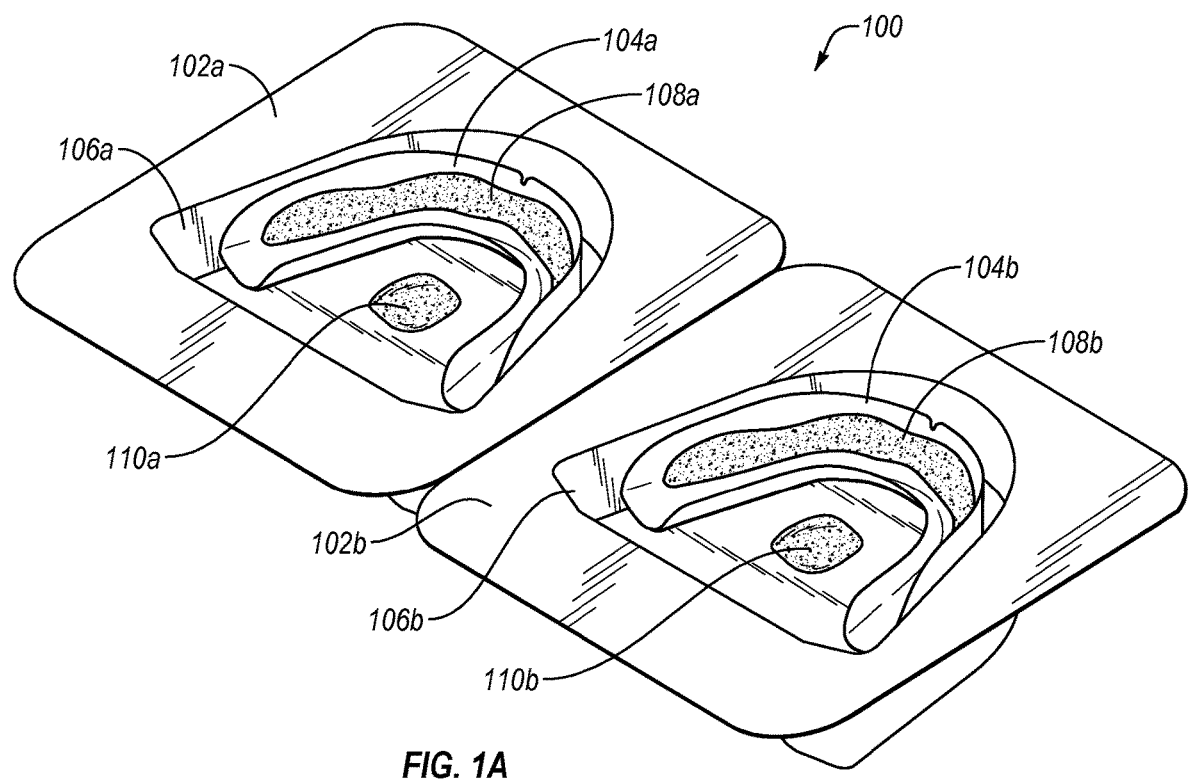
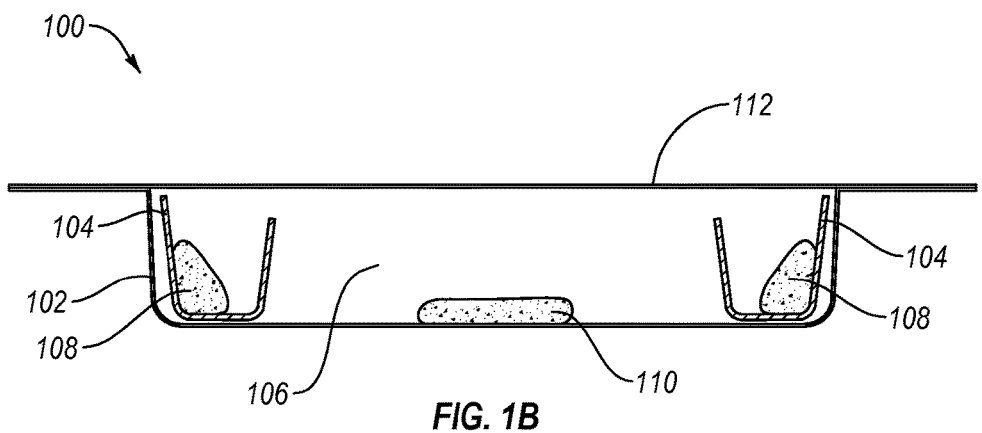
FIG. 1A
FIG. 1B

PACKAGING SYSTEMS INCLUDING SACRIFICIAL COMPOSITION

BACKGROUND OF THE INVENTION

1. The Field of the Invention

The present invention is in the field of packaging systems, more particularly sealable packaging containers for improving or maintaining stability of a composition.

2. The Relevant Technology

A wide variety of compositions and appliances are used to provide desired treatments to a patient, including a patient's teeth. The composition may be a treatment composition that includes one or more active agents. Alternatively, the composition may be an adhesive or other composition that may dry out or cure when exposed to air. Some compositions include at least one volatile material, such as a solvent or polymerizable liquid. These or other compositions may include at least one gas-releasing material, such as peroxide compositions used to whiten a person's teeth.

In many cases it may be important or desirable to maintain at least a minimum amount of stability of a composition over time (e.g., during storage after manufacture and prior to use). Stability is often maintained by keeping the composition within a sealed container. The sealed container may prevent the composition from drying out, such as by evaporation of a volatile solvent. Alternatively, the sealed container may keep oxygen or air from contacting the composition. In some cases, the sealed container may prevent or slow down decomposition of a gas-releasing material, such as peroxide, which releases oxygen as it decomposes.

Stability is typically maintained when the sealed container is able to maintain a vacuum and/or prevent evaporation of volatile components and/or prevent decomposition of gas-releasing materials. Some containers, such as glass bottles with plastic or metal screw caps, are able to maintain a high level of stability because they are highly impervious to air, oxygen, other gases, moisture, or volatile materials.

In some cases it may be desirable to manufacture dental whitening trays, dental whitening strips, other dental appliances, or other devices with compositions applied thereto and store them in lightweight disposable packing containers. An example of a common lightweight disposable packing container is a molded polymer container body for holding therein a device and composition and metal foil or other peelable sheet that covers an opening of the molded polymer container body to form a sealed interior volume within which the device and composition are stored after manufacture and prior to use.

A disadvantage of lightweight disposable packing containers is that they may not be completely impervious to air, oxygen, other gases, moisture, and/or volatile materials. And even if they are substantially impervious to air, oxygen, other gases, moisture, and/or volatile materials, some amount of water, volatile material or released gas may collect within the sealed interior volume after packaging and prior to breaking the seal, which may reduce the stability and/or expected potency of the composition.

Because of problems associated with lost potency, it is sometimes recommended that pre-filled whitening systems be stored in a refrigerated environment prior to use. Refrigerated storage slows or prevents decomposition peroxide whitening agents, which maintains potency and extends the shelf life of the packaged product. Refrigerated storage is often impractical, however, particularly for dental treatment systems that are intended for over-the-counter sale where refrigerated shelving may not be available or practical.

SUMMARY OF THE INVENTION

Disclosed herein are packaging systems for improving long-term stability and shelf-life of a composition stored therein. According to several embodiments, packaging systems include a packaging container defining a sealed or sealable interior volume. For example, the packaging container may include a removable cover, and may be formed from one or more materials that are substantially impervious to at least one of air, oxygen, other gases, moisture, or volatile material. A main composition and a sacrificial composition may be positioned within the sealed or sealable interior volume.

According to one embodiment, the sealable or sealed interior volume may include a first compartment having a shape for storing therein an appliance and a main composition comprising at least one volatile or gas-releasing material and a second compartment or region in fluid communication with the first compartment for storing therein a sacrificial composition comprising at least one volatile or gas-releasing material.

According to several embodiments, the packaging container and/or removable cover may have a laminate structure composed of at least one barrier layer that is substantially impervious to at least one of air, oxygen, other gases, moisture, or volatile material and at least one structural layer that provides strength and/or rigidity to the laminate structure.

According to several embodiments, the packaging system is designed to hold therein a dental appliance. According one embodiment, the dental appliance is a dental treatment device that includes a barrier layer in the shape of a tray or strip and a dental treatment composition having an active agent, such as a dental bleaching agent. According one embodiment, the dental appliance is an orthodontic appliance and the main composition is a dental adhesive or composite.

These and other benefits, advantages and features of the present invention will become more full apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 1A schematically illustrates an exemplary packaging container for use with a removable cover to form a packaging system for improving long-term stability of a composition stored within the packaging system;

FIG. 1B is a cross-sectional view of the packaging container of FIG. 1A with a removable cover to form a packaging system for improving long-term stability of a composition stored within the packaging system;

DETAILED DESCRIPTION OF THE PREFERRED EMBODIMENTS

Figure 2A:
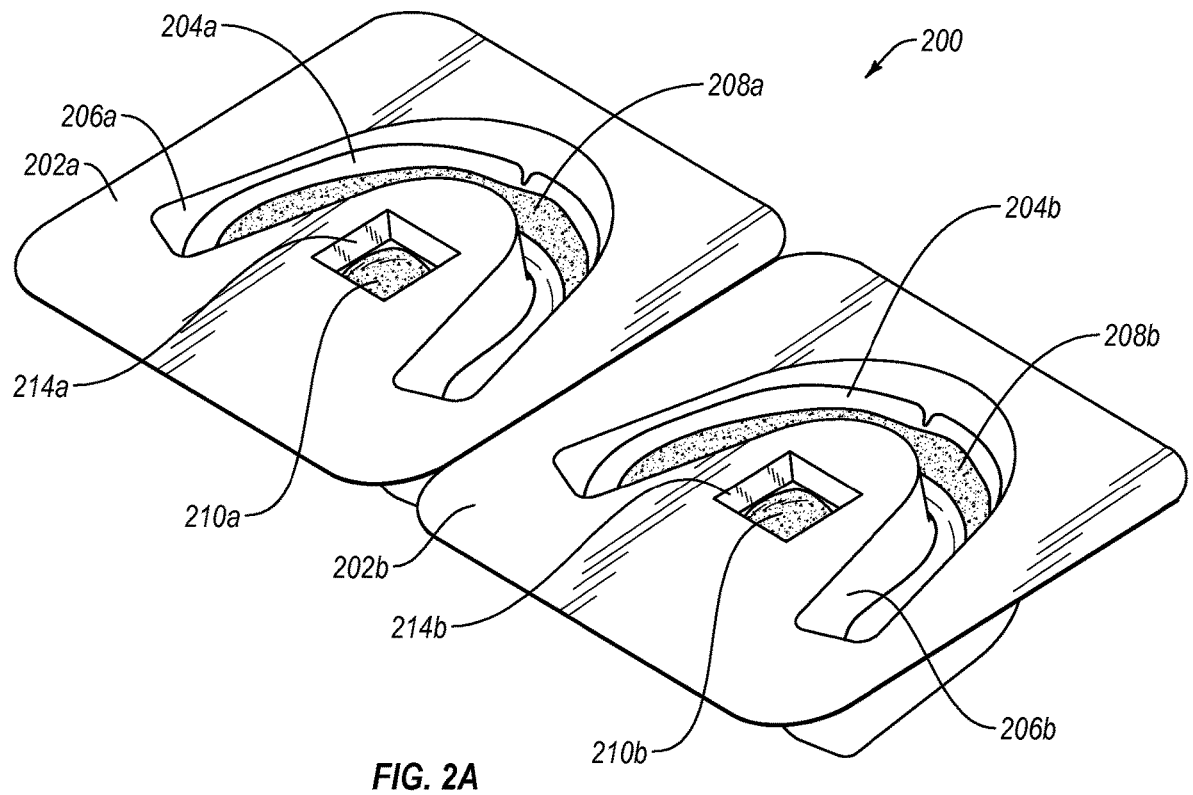
FIG. 2A schematically illustrates an alternative exemplary packaging container for use with a removable cover to form a packaging system for improving long-term stability of a composition stored within the packaging system.

Disclosed herein are packaging systems for maintaining stability of a composition over time. In general, such packaging systems may include a packaging container defining a sealable or sealed interior volume. As a non-limiting example, the packaging container may include a removable cover, and the packaging container and the removable cover may include one or more materials that are or semi-pervious or substantially impervious to at least one of air, oxygen, other gases, moisture, or volatile material. A main composition and a sacrificial composition are or may be positioned within the sealed or sealable interior volume.

The main composition may include one or more volatile and/or gas-releasing materials that may volatilize and/or release gas, resulting in reduced concentration of the one or more volatile and/or gas-releasing materials, decreased stability and/or loss of potency of the composition. Even in a sealed container, the release of materials, such as volatile compounds and/or gases, from the main composition may proceed until a partial pressure of such materials within the sealed interior volume reaches equilibrium and release of such materials is no longer thermodynamically favored. To accelerate equilibrium and prevent or reduce the release of volatile materials and/or gases from the main composition, the sacrificial composition may be configured to similar molecules in as a gas or vapor to increase the amount of ambient molecules the sealed interior volume. An amount of volatile materials and/or gas released from the sacrificial composition into the sealed interior may generally correspond to an amount of such volatile materials and/or gas that would otherwise be released from the main composition in the absence of the sacrificial composition. In other words, the more of such volatile materials and/or gas released from the sacrificial composition up and until equilibrium is reached within the sealed interior volume, the less of such volatile materials and/or gas that will be released by the main composition. In this way, the stability and/or concentrations of volatile and/or gas-releasing materials in the main composition may be maintained and the shelf-life of the main composition may be increased over time by including the sacrificial composition in the sealed interior volume housing the main composition.

Without being bound to any particular theory, it is believed that a volatile or gas-releasing material is able to vaporize, sublimate or emit gas so long as the partial pressure of the vapor or gas in the immediately surrounding atmosphere in a confined volume is below the equilibrium partial pressure for the particular vapor or gas at a given temperature and pressure. The partial pressure of a vapor or gas released from the main composition within a confined volume (e.g., a sealed interior volume or headspace within a packaging system) may initially be small or non-existent when the composition is first packaged within the confined volume. This increases the propensity of such vapor or gas to be lost from the main composition, which may reduce stability and/or potency of the main composition. Including the sacrificial composition configured to emit a vapor or gas within, or in fluid communication with, the sealed interior volume may substantially reduce or eliminate the amount of volatile or gas-releasing material released from the main composition to achieve equilibrium partial pressure within the sealed interior volume. The sacrificial component may include any volatile and/or gas releasing material having a vapor pressure greater than or equal to that of the volatile and/or gas releasing material contained in the main composition. As a non-limiting example, the vapor or gas emitted by the sacrificial composition may be the same or similar to that released by the main composition. This, in turn, reduces the amount of such vapor or gas that might otherwise be lost from the main composition in the absence of the sacrificial composition.

According to an embodiment, the sealable or sealed interior volume may include different compartments or regions that are nevertheless in fluid (e.g., gaseous) communication. In this way, gases or vapors from one compartment or region may be transmitted to another compartment or region in fluid communication such that the compartments reach equilibrium relative to such gases or vapors. According to an embodiment, the sealable or sealed interior volume may include a first compartment having a shape for storing therein an appliance and a main composition comprising at least one volatile or gas-releasing material and a second compartment or region in fluid communication with the first compartment for storing therein a sacrificial composition comprising at least one volatile or gas-releasing material. Providing a compartment having a shape and size that closely matches the shape and size of the appliance may greatly reduce the size of the sealed interior volume or headspace within the packaging system.

According to another embodiment, the second compartment or region may provide a well for storing therein, or a designated space for storing therein, a measured quantity of a sacrificial composition comprising at least one volatile or gas-releasing material. Providing a second compartment having a well or designated space for placing an amount of the sacrificial composition may also reduce the size of the sealed interior volume or headspace within the packaging system.

The term "sealable interior volume" refers to a volume within a packaging system that may be sealed to form a sealed interior volume.

The term "sealed interior volume" refers to a volume within a packaging system into which one or more appliances, one or more main compositions, and one or more sacrificial compositions may be placed. The sealed interior volume may include a "main composition volume" and "headspace."

The term "composition volume" refers to the cumulative volume of the one or more main compositions and one or more sacrificial compositions within a sealed interior volume.

The term "headspace" generally refers to a remaining volume within the sealed interior volume that is not occupied by an appliance, the one or more main compositions, and the one or more sacrificial compositions, and into which vapors or gases emitted by the main and/or sacrificial composition may collect.

The term "stability-affecting component" refers to a material or component within the main composition that affects or relates to the stability of the main composition. The stability-affecting component may be a material which is initially contained within the main composition when initially manufactured and packaged but which can be lost from the main composition over time by evaporation, sublimation or decomposition to release gas, in which loss of such material reduces stability.

The term "stabilizing component" refers to a material or component that acts to stabilize the stability-affecting component within the main composition. For example, the stabilizing component may stabilize the main composition by replacing volatile components within the main composition or displacing volatile components within the sealed interior volume or headspace of a package. The stabilizing component may be any volatile substance (whether contained within the main composition or not) having a vaporization rate greater than or equal to that of the volatile components within the main composition. The stabilizing component may be the same component, a similar component, or a different component than the stability-affecting component. The sacrificial composition may be formulated such that the stabilizing component releases vapor or gas into the sealed interior volume at a rate greater than or equal to a rate at which the main composition releases vapor or gas to reduce or eliminate loss of the stability-affecting components from the main composition.

The term "stability" as used herein refers to a propensity of a composition to maintain desired properties, as potency, efficacy, concentration of active ingredients, rheology, homogeneity, reactivity, adhesiveness, and the like, over a period of time, and includes both chemical stability and physical stability of the composition over the period of time. The term "physical stability" refers to maintaining the physical form of an active component, such as a peroxide, within the composition. The term "chemical stability" refers to maintaining concentrations and potency of the active component within the composition.

The term "equilibrium partial pressure" refers to the partial pressure of a vapor or gas at which no significant amounts of such vapor or gas are emitted by a main composition and/or sacrificial composition at a given temperature and pressure within a confined volume.

The term "potency" as used herein refers to the concentration and/or total quantity of an active agent within a composition. To the extent that a composition contains an initial concentration and/or total quantity of active agent, the potency may be measured by or is related to the concentration and/or total quantity of the active agent over a given time period.

The term "reactivity" refers to the ability of a composition to undergo a chemical reaction, such as when exposed to air and/or mixed with an activating agent. Premature exposure to air or other deleterious substances may reduce the reactivity of a composition and/or cause the composition to react or degrade prematurely, thereby reducing its ability to further react, or react fully, when it is placed into use.

The term "rheology" as used herein refers to the flow properties of a composition. Examples of different rheologies include, but are not limited to, fluid, gel, sticky and viscous gel, putty or putty-like, and substantially solid. The term "main composition" as used herein refers to one or more compositions contained or packaged within the sealed or sealable interior volume of a storage system for which it is desired to maintain stability over time prior to use. The main composition typically includes at least one volatile and/or gas-releasing component that, if released from the composition, causes the composition to lose stability. The main composition may have a desired rheology, such as fluid, gel, sticky and viscous gel, putty or putty-like, or substantially solid. In the case where there are multiple main compositions storied within a sealed interior volume of a packaging system, they may have similar or different rheologies.

The term "volatile material" as used herein refers to a material, which may be a liquid, fluid or solid, having one or more volatile components with a sufficiently high vapor pressure to be separated from a solid as a vapor at room temperature. Such volatile components may evaporate or sublimate at room temperature. Examples of volatile materials include, but are not limited to, water, organic liquid solvents, polar solvents, including but not limited to lower alcohols, alkanes, alkenes, aldehydes, ketones, ethers, esters, acetals, ketals, carboxylic acids, and chlorinated hydrocarbons, and liquid or low molecular weight monomers used in light or chemical cure adhesives, such as triethylene glycol methacrylate (TEGMA).

The term "gas-releasing material" includes solid, fluid or liquid substances that reversibly or irreversibly decompose to release a gas. Examples include peroxides, such as hydrogen peroxide, carbamide peroxide, calcium peroxide, and sodium perborate.

The term "sacrificial composition" as used herein refers to one or more compositions contained or packaged within a sealed or sealable interior volume of a storage system, typically in fluid or gaseous communication with one or more main compositions. Such sacrificial compositions may include one or more stabilizing components, which may be volatile or gas-releasing materials having a greater vaporization rate than the volatile or gas-releasing materials contained in the one or more main compositions. For example, the sacrificial composition may be formulated to release vapors or gases into a sealed interior volume or headspace surrounding the main composition, thereby providing an increase in the partial pressure of such vapors and gases within the sealed interior volume or headspace. Such an increase in the partial pressure may substantially reduce or eliminate generation of vapors and gases from the main composition. By increasing the rate at which an equilibrium partial pressure of one or more vapors or gases of interest is achieved, the sacrificial composition improves the stability of the main composition, which might otherwise lose a greater quantity of the one or more vapors or gases in the absence of the sacrificial composition.

The sacrificial composition may be the same or different than the main composition. In some cases, the sacrificial composition will simply be the same composition as the main composition, which reduces the number of different compositions required to manufacture a pre-packaged appliance. Alternatively, the sacrificial composition may omit one or more components from the main composition so as to reduce needless cost of such compositions and/or increase the quantity or concentration of the vapor forming or gas-releasing material used to maintain or increase stability of the main composition. Where there are different main compositions in a confined volume which emit different types and/or amounts of vapor or gas, there may be multiple corresponding sacrificial compositions that are able to emit a corresponding vapor or gas in order to increase or maintain the stability of each main composition. The sacrificial composition may have the same or different rheology as the main composition. For example, the sacrificial composition may have a liquid, gel or solid form. For ease of manufacture, the sacrificial composition might contain a preformed shape, such as a pellet, tablet, cube, disc, or flat sheet, which may be placed in a well or adhered to an interior wall of the packaging system in order to be in fluid communication with the main composition. Additionally, the sacrificial composition may be positioned within a permeable or semipermeable packet or pouch, which may be placed in a region of the packaging system in fluid communication with the main composition. As a non-limiting example, the packaging system may be a plastic or foil pouch and the sacrificial composition may be positioned in the pouch in the form of a tablet, within a well or within a semipermeable membrane.

According to embodiments of the disclosure, for a given component of a main composition that may affect the stability of the main composition, such as a volatile or gas-releasing material, the concentration of the same or similar component in a corresponding sacrificial composition may be less than, the same as, or greater than the concentration of that component in the main composition. According to embodiments as disclosed herein, the concentration of a given component in a sacrificial composition may be at least about 50% of the concentration of that component in the main composition, preferably at least about 75%, more preferably at least about 100%, and most preferably at least about 125% of the concentration of that component in the main composition. In some cases, the concentration of the given component in the sacrificial composition may be in a range of about 50% to about 500%, or about 75% to about 400%, about 100% to about 300%, or about 125% to about 250% of the concentration of the same or similar component in the main composition.

It should be understood that, in some cases, the stability-affecting component may be influenced by the presence of similar components in the confined volume or headspace. For example, the buildup of partial pressure of a volatile solvent may help a similar, but not identical volatile solvent, reach equilibrium within the confined volume or headspace (e.g., acetone and methylethyl ketone).

Similarly, where a gas-releasing material in the main composition decomposes to release a specific gas (e.g., oxygen), the sacrificial composition may include a different gas-releasing material as long as the gas that is released (e.g., oxygen) helps the confined volume or headspace reach equilibrium for that gas more quickly. For example, the main composition may include a stabilized peroxide whitening agent that releases oxygen slowly over time, while the sacrificial composition may include a less stable peroxide or other oxygen-releasing component that releases oxygen at an increased rate in comparison to the main composition, causing the confined volume or headspace to more quickly reach an equilibrium partial pressure of oxygen within the confined volume. Where the packaging material defining the confined headspace is advantageously made from a combination of materials that is impermeable to air, oxygen, other gases, moisture, and/or volatile materials, once equilibrium for a particular material is reached, essentially no more of that material will be emitted by either the main composition or the sacrificial composition.

Instead of concentration, another point of comparison might be the rate at which the main and sacrificial compositions are able to emit or lose a given vapor or gas within a given time period. According to embodiments of the invention, the main and sacrificial compositions may include a given volatile or gas-releasing component that may vaporize and/or release gas within the sealed interior volume or headspace, wherein the sacrificial composition is configured to vaporize and/or emit vapors or gases at a rate greater than or equal to the main composition. For example, the sacrificial composition may vaporize and/or emit gas at a rate that is at least about 100% of the rate at which the same or similar component vaporizes or is emitted by the main composition, or at a rate that is at least about 125%, at least about 150%, at least about 175%, at least about 200%, at least about 250%, at least about 300%, at least about 400%, or at least about 500% of the rate at which the same, similar or different vapor or gas is emitted by the main composition.

Embodiments of packaging systems disclosed herein are useful for maintaining the concentration of an active agent (e.g., peroxide) within a desired concentration range relative to an initial concentration of the active agent when initially placed within a sealed interior volume, wherein the desired concentration is at least about 75% of the initial concentration after at least 3 months, preferably at least about 85% of the initial concentration after at least 3 months, more preferably at least about 90% of the initial concentration after at least 3 months, and most preferably in a range of about 95% to about 100% of the initial concentration after at least 3 months.

By way of example and not limitation, the materials used to make the packaging systems as disclosed herein may be selected to be substantially impervious to the one or more given volatiles or gases released from the main composition. In many cases, the one or more packaging system materials will be selected so as to be substantially impervious to at least one of air, oxygen, water vapor, volatile organic solvent, or volatile material. In addition, the packaging system may include materials whose main purpose is to provide additional strength and/or rigidity to the packaging system.

Examples of materials that provide a good barrier to oxygen molecules (i.e., have low permeability to oxygen molecules) include ethylene-vinyl alcohol copolymer (EVOH), propylene-vinyl alcohol copolymer (PVOH), polyvinylidene chloride (PVDC), polyamides, nylons (e.g., types 6 and 66), nitrile copolymers, polyacrylonitriles (PAN), polyethylene terephthalate (PET), resorcinol, ORMOCER hybrid polymers, liquid crystal polymers (LCPs), aliphatic polyketones, plasma glass coatings, thermoset epoxy coatings, and nanocomposites.

Examples of materials that provide a good barrier to water molecules (i.e., have low permeability to water molecules) include cyclic olefin polymers (COPs), cyclic olefin copolymers (COCs), polychlorotrifluoroethylene (PCTFE), aluminum oxide coatings (AlOx), vinylidene chloride copolymers, high density polyethylene (HDPE), and polypropylene.

Examples of materials that provide a good barrier to oxygen, water, air and volatile materials include metal foils, such as aluminum foil.

In addition to the foregoing, various polymer layers may be included to provide additional strength and/or rigidity to the packaging system. In addition, some of these materials may increase the barrier properties of the overall packaging system relative to oxygen, water, air and volatile materials. Because volatile organic molecules are much larger than oxygen and water molecules, while air molecules are typically about the same size, providing a good barrier to either or both of oxygen and water molecules should result in a good barrier to both air and especially volatile organic molecules (at least as long as the materials are not damaged in the presence of a particular organic solvent used in a composition).

Structural polymers, which may or may not enhance the barrier properties of the packaging system include, but are not limited to, polyolefins, polyesters, polypropylene (PP), polyethylene (PE), polyvinylchloride (PVC), polyvinylidichloride (PVDC), ethylene-vinyl acetate copolymer (EVA), and glycol-modified polyethylene terephthalate (PETG). Polypropylene is easily bondable to COC, provides structure and bulk to the laminate polymer film, and is relatively inexpensive.

The layers may be co-extruded, using the heat of the extrusion process to bond the layers together, or the layers may be bonded together by use of suitable adhesives.

The packaging systems may be manufactured to have a size and shape that approximately corresponds to the size and shape of the appliance in order to reduce headspace and confine the appliance without excessive movement or shaking. The interior volume of a packaging system may also be selected to minimize headspace and thereby minimize the headspace within which vapors and/or gases released from the main and sacrificial compositions may collect. Minimizing the absolute volume of the headspace minimizes the absolute quantity of vapors and/or gases that must collect within the sealed interior volume before equilibrium is reached relative to a given stabilizing component.

Within a sealed interior volume of a packaging system, part of the volume will comprise the cumulative volumes of the one or more main compositions and the one or more sacrificial compositions (collectively, the "composition volume"). A portion of the sealed interior volume is empty space (or "headspace") (i.e., the portion of the sealed interior volume not occupied by the one or more appliances, the one or more main compositions, and the one or more sacrificial compositions) into which vapors and/or gases released from the main and sacrificial compositions may collect. Reducing the ratio of "headspace" to "composition volume" correspondingly reduces the amount of vapor or gas that is released by the main and sacrificial compositions before equilibrium is reached relative to the volatile component(s) within the main composition.

According to several embodiments, the headspace within the sealed or sealable interior volume may be less than about 500% of the composition volume, preferably less than about 400%, more preferably less than about 300%, and most preferably less than about 200% of the composition volume.

Reference is now made to the drawings. FIGS. 1A and 1B illustrate an exemplary packaging system 100 for use in maintaining the stability of an oral treatment composition. Packaging system 100 includes a first container 102*a* and a second container 102*b*, which are designed to hold therein first and second oral appliances (e.g., oral treatment trays) 104*a*, 104*b* within first and second appliance wells or compartments 106*a*, 106*b*, respectively. Appliance wells or compartments 106 are advantageously configured to hold appliances 104 in a manner that minimized movement and also reduces a ratio of headspace to respect to composition volume.

It will be appreciated that any number of containers may be included, which may be attached together as shown or packaged individually without connection, such as by stacking within a bulk container. While packaging system 100 for an oral treatment trays are illustrated herein, it should be recognized that the packaging system 100 may have any shape or configuration defining an enclosed volume, such as a bag, box, bottle, dispenser, case, and the like. Two containers 102 are shown in FIG. 1A in order to provide an oral treatment kit that includes two dental treatment trays 104 (e.g., for individually treating upper and lower dental arches).

First and second dental treatment trays 104*a*, 104*b* each include first and second dental compositions 108*a*, 108*b*, disposed within corresponding troughs of the dental treatment trays 104*a*, 104*b*, respectively. The dental compositions 108*a*, 108*b* may be considered to be one or more "main compositions" which contain one or more stability-affecting components which may include, for example, volatile components, such as liquids or solvents that may evaporate and form a vapor within a confined space, or a gas-releasing material, such as a peroxide or other active agent that may release gas a result of decomposition. The dental compositions 108*a*, 108*b* may be the same or different, may contain the same or different types of stability-affecting components, and/or may contain the same or different amount or concentrations of stability-affecting components.

The packaging system 100 further includes a first sacrificial composition 110*a* disposed within a region of first appliance well or compartment 106*a* in order to be in fluid (e.g., gaseous) communication with first dental composition 108*a*, and a second sacrificial composition 110*b* disposed within a region of second appliance well or compartment 106*b* in order to be in fluid (e.g., gaseous) communication with second dental composition 108*b*. While the sacrificial compositions 110*a*, 110*b* are illustrated as being disposed substantially in a center of the packaging system 100, it is to be understood that the sacrificial compositions 110*a*, 110*b* may be disposed in any position within the packaging system 100 in which the sacrificial compositions 110*a*, 110*b* are in fluid communication with the dental compositions 108*a*, 108*b*. In addition, the sacrificial compositions 110*a*, 110*b* may be partially or entirely enveloped by a material permeable to the vapors and/or gases.

The sacrificial compositions 110*a*, 110*b* may include one or more stabilizing components. For example, the sacrificial compositions 110*a*, 100*b* may be the same as dental treatment compositions 108*a*, 108*b*, may at least contain the same or similar stability-affecting components as dental treatment compositions 108*a*, 108*b*, or may contain a stabilizing component having a vaporization rate greater than or equal to the dental compositions 108*a*, 108*b*, respectively. The sacrificial compositions 110*a*, 110*b* may contain liquids or solvents that may evaporate and form a vapor within a confined space, or a gas-releasing material, such as peroxides or other active agent that may release gas a result of decomposition. The sacrificial compositions 110*a*, 110*b* may be the same or different, may contain the same or different types of stabilizing components, and/or may contain the same or different amount or concentration of the stabilizing component(s).

As shown in FIG. 1B, packaging system 100 further includes a removable cover 112, which may be formed from one or more materials that are substantially impervious to at least one of air, oxygen, other gases, moisture, or volatile materials, which forms a seal with packaging container 102 when bonded or adhered thereto, and yields a sealed interior volume corresponding to the size of appliance well or compartment 106. By way of example, removable cover 112 may include an opaque foil material. The container 102 may itself be opaque, or it may be transparent or translucent. The sealed interior volume of packaging system 100 maintains dental composition 108 and sacrificial composition 110 in fluid (e.g., gaseous) communication during storage so that sacrificial composition 110 may help maintain the stability of dental treatment composition 108 prior to use, thus extending the shelf-life of the dental composition 108.

The dental composition 108 may include any composition susceptible to destabilization or dehydration, such as a desired type of treatment agent. For example, the treatment agent may comprise one or more of a dental bleaching agent; a desensitizing agent (e.g., potassium nitrate, other potassium salts, citric acid, citrates, or sodium fluoride); a remineralizing agent (e.g., sodium fluoride, stannous fluoride, sodium monofluorophosphate, or other fluoride salts); antimicrobial agents (e.g., chlorhexidine, triclosan, sodium benzoate, parabens, tetracycline, phenols, or cetyl pyridinium chloride); an anti-plaque agent; an anti-tartar agent (e.g., pyrophosphates); a gingival soothing agent (e.g., aloe vera, mild potassium nitrate, or isotonic solution-forming salts); an anesthetic (e.g., benzocaine, lidocaine, or the like); an anti-oxidant (e.g., vitamin A, vitamin C, vitamin E, other vitamins, or carotene); or a mouth freshening agent (e.g., camphor or wintergreen).

Examples of dental bleaching agents include, but are not limited to, one or more of aqueous hydrogen peroxide, carbamide peroxide, metal perborates (e.g., sodium perborate), metal percarbonates (e.g., sodium percarbonate), metal peroxides (e.g., calcium peroxide), metal chlorites or hypochlorites, peroxy acids (e.g., peroxyacetic acid), or peroxy acid salts.

The dental composition 108 may also include a thickening agent, such as hydrophilic polymers. Examples of hydrophilic polymer thickening agents include, but are not limited to, polyvinyl pyrrolidone (PVP), PVP-vinyl acetate copolymers, carboxypolymethylene (e.g., CARBOPOL, sold by Novean, Inc.), polyethylene oxide (e.g., POLYOX, made by Union Carbide), polyacrylic acid polymers or copolymers (e.g., PEMULEN, sold by Novean, Inc.), polyacrylates, polyacrylamides, copolymers of polyacrylic acid and polyacrylamide, carboxymethylcellulose, carboxypropylcellulose, cellulosic ethers, polysaccharide gums, proteins, or the like.

The dental composition 108 may also include liquid carrier materials, including one or more volatile liquids, such as water, alcohol, or acetone, which may evaporate and cause the dental composition 108 to prematurely dry out or stiffen. In addition, if a peroxide is included, treatment composition 108 may lose potency to the extent the peroxide is permitted to decompose and release oxygen. For example, hydrogen peroxide may decompose to form water and oxygen. Packaging system 100 is therefore advantageously made from one or more materials that prevent drying out and/or deactivation of the dental composition 108. As a non-limiting example, at least a portion of the container 102 may be formed of a laminate polymer material that is substantially impervious to oxygen molecules, water molecules, other gases, and/or volatile solvents. The container may have a wall thickness in a range of about 0.006" (6 mils) to about 0.030" (30 mils), or about 0.012" to about 0.028", or about 0.015" to about 0.025".

Alternatively, dental composition 108 may be an adhesive, composite or other reactive material for use with an oral appliance, which includes a volatile solvent and/or one or more polymerizable materials. In such case main composition 108 may lose stability if permitted to dry out by evaporation of a volatile liquid or solvent and/or prematurely react in the presence of air or oxygen. In addition, the polymerizable material may comprise one or more volatile monomers, such as TEGMA, which may evaporate from the adhesive and reduce reactivity or adhesive strength.

The sacrificial composition 110 may be a sticky, viscous gel, putty, or substantially solid composition in order to remain in place and not flow onto appliance 104 during storage. As a non-limiting example, the sacrificial composition 110 may additionally be formed as a solid tablet, pellet or sheet, or may be positioned within packet or wrapper formed from a permeable or semi-permeable material.

Figure 2B:
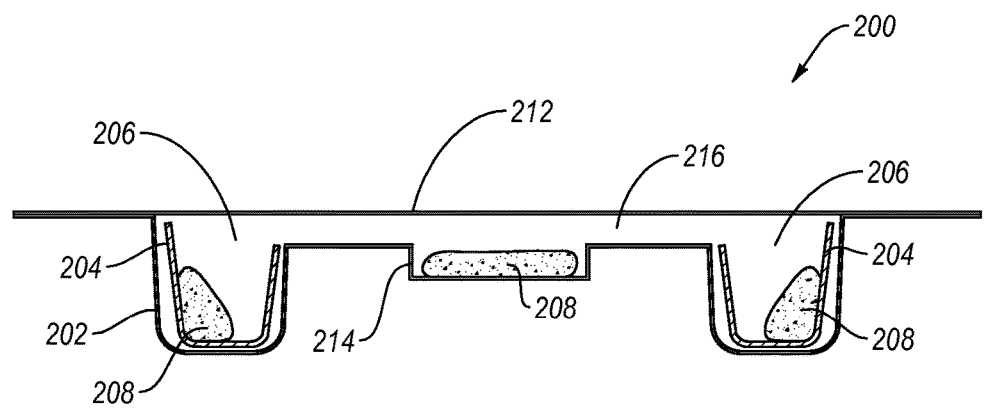
FIG. 2B is a cross-sectional view of the packaging container of FIG. 2A with a removable cover to form a packaging system for improving long-term stability of a composition stored within the packaging system.
Figure 2C:
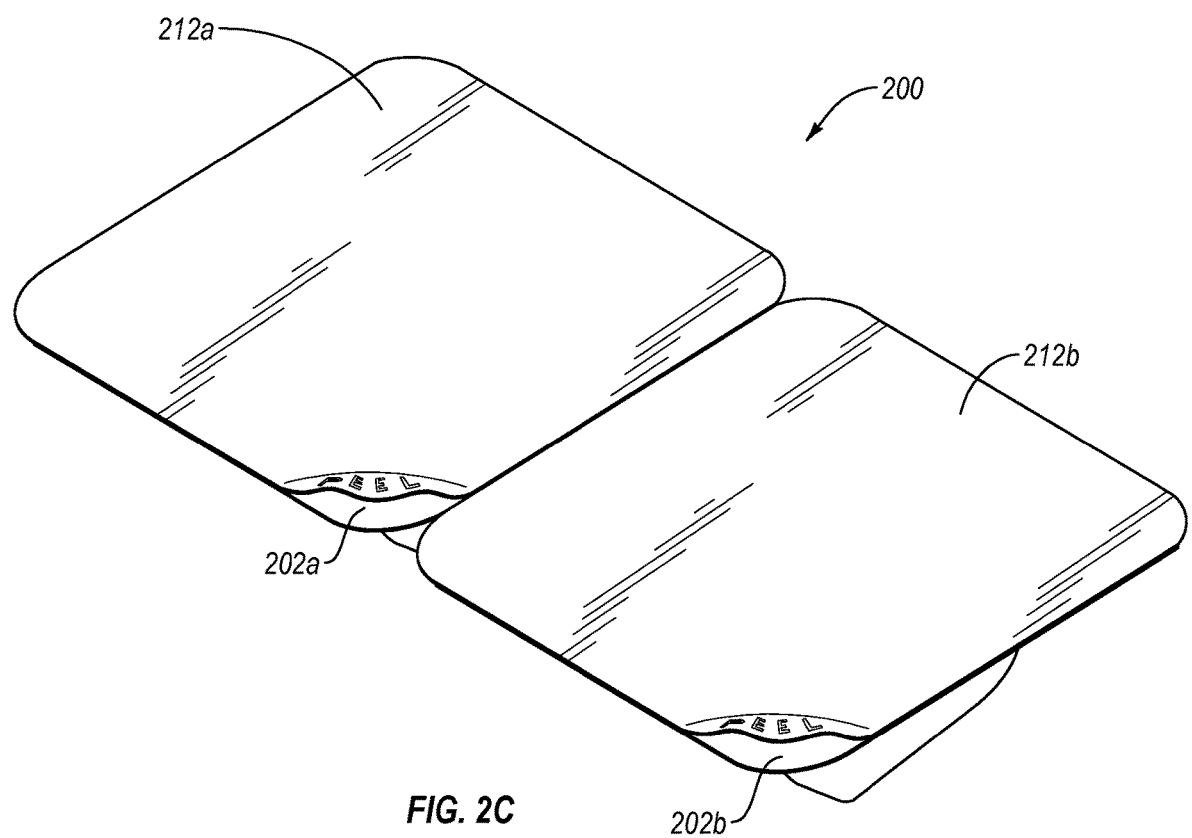
FIG. 2C is a perspective view of the packaging system of FIG. 2B.

FIGS. 2A-2C illustrate an exemplary packaging system 200 for use in maintaining the stability of an oral treatment composition. Packaging system 200 includes a first container 202a and a second container 202b, which are designed to hold therein first and second oral appliances (e.g., oral treatment trays) 204a, 204b within first and second appliance wells or compartments 206a, 206b, respectively. The appliance wells or compartments 206 are advantageously configured to hold the appliances 204 in a manner that minimizes movement and also reduces headspace.

It will be appreciated that any number of containers may be included, which may be attached together as shown or packaged individually without connection, such as by stacking within a bulk container. Two containers 202 are shown in FIG. 2A in order to provide an oral treatment kit that includes two oral treatment trays 204 (e.g., for individually treating upper and lower dental arches).

First and second oral treatment trays 204a, 204b include first and second oral treatment compositions 208a, 208b disposed within corresponding troughs of treatment trays 204a, 204b, respectively. The oral treatment compositions 208a, 208b may be considered to be one or more "main compositions" which contain one or stability-affecting, such as liquids or solvents that may evaporate and form a vapor within a confined space, or a gas-releasing material, such as a peroxide or other active agent that may release gas a result of decomposition or reaction with another component within the main composition. The main compositions 208a, 208b may be the same or different, may contain the same or different types of stabilizing, and/or may contain the same or different amount or concentrations of the stabilizing component(s).

The packaging system 200 further includes a first sacrificial composition 210a disposed within a first auxiliary well or compartment 214a in order to be in fluid (e.g., gaseous) communication with first oral treatment composition 208a, and a second sacrificial composition 210b disposed within second auxiliary well or compartment 214b in order to be in fluid (e.g., gaseous) communication with second oral treatment composition 208b. The sacrificial compositions 210a, 210b may be formed in as a liquid, gel or solid, and may partially or completely fill the auxiliary wells or compartments 214a, 214b, respectively.

While the auxiliary wells or compartments 214a, 214b are illustrated as being formed in a surface of the containers 202a, 202b, respectively, it is to be understood that the auxiliary wells or compartments 214a, 214b may have any other configuration that positions the sacrificial compositions 210a, 210b in fluid communication with the main composition 208a, 208b. As a non-limiting example, the auxiliary wells 214a, 214b may include upper and lower surfaces and an aperture or passageway that exposes the sacrificial compositions 210a, 210b may be formed in one or more sidewalls of the auxiliary wells 214a, 214b. As another non-limiting example, a material permeable to the vapors and/or gases released by the sacrificial compositions 210a, 210b may be used to cover the auxiliary wells 214a, 214b or to enclose the sacrificial compositions 210a, 210b.

While the sacrificial compositions 210a, 210b are illustrated in FIGS. 2A and 2B as being disposed within the auxiliary wells or compartments 214a, 214b, it is to be understood that the sacrificial compositions 210a, 210b may be disposed in any position within the packaging system 200. For example, the sacrificial compositions 210a, 210b may be positioned within the appliance wells or compartments 206a, 206b, such as beneath the first and second treatment trays 204a, 204b, respectively, and may optionally be covered by a permeable material.

The sacrificial compositions 210a, 210b may be the same as treatment compositions 208a, 208b, may at least contain the same or similar stability-affecting components as treatment compositions 208a, 208b, or may contain a component having a vaporization rate greater than or equal to the dental compositions 208a, 208b, respectively. The sacrificial compositions 210a, 210b may contain liquids or solvents that may evaporate and form a vapor within a confined space, or a gas-releasing material, such as a peroxide or other active agent that may release gas a result of decomposition or reaction with another component within the sacrificial composition 210a, 2210b. The sacrificial compositions 210a, 210b may be the same or different, may contain the same or different types of stability-affecting components, and/or may contain the same or different amount or concentrations of the stability-affecting component(s).

As shown in FIG. 2B, the packaging system 200 further includes a removable cover 212, which may be formed from one or more materials that are substantially impervious to at least one of air, oxygen, other gases, moisture, or volatile materials, which forms a seal with the packaging container 202 when bonded or adhered thereto, and yields a sealed interior volume corresponding to the combined volumes of the appliance well or compartment 206, the auxiliary well or compartment 214, and the bridging region 216. The sealed interior volume of the packaging system 200 maintains the treatment composition 208 and the sacrificial composition 210 in fluid (e.g., gaseous) communication during storage so that the sacrificial composition 210 may help maintain the stability of the treatment composition 208 prior to use. The combination of the appliance well or compartment 206, the auxiliary well or compartment 214 and the bridging region 216 has the effect of further reducing headspace in this embodiment compared to the headspace of the packaging system 100 of FIGS. 2A and 2B. Stated another way, they may reduce the ratio of headspace to composition volume.

As seen in FIG. 2C, removable cover 212a, 212b, which may include an opaque foil material, may be peelable covers. Prior to removal, removable covers 212a, 212b enclosed and thereby protect some or all of upper walls of the containers 202a, 202b. This enables the packaging system 200 to be stacked and stored as desired while maintaining cleanliness.

Figure 3A:
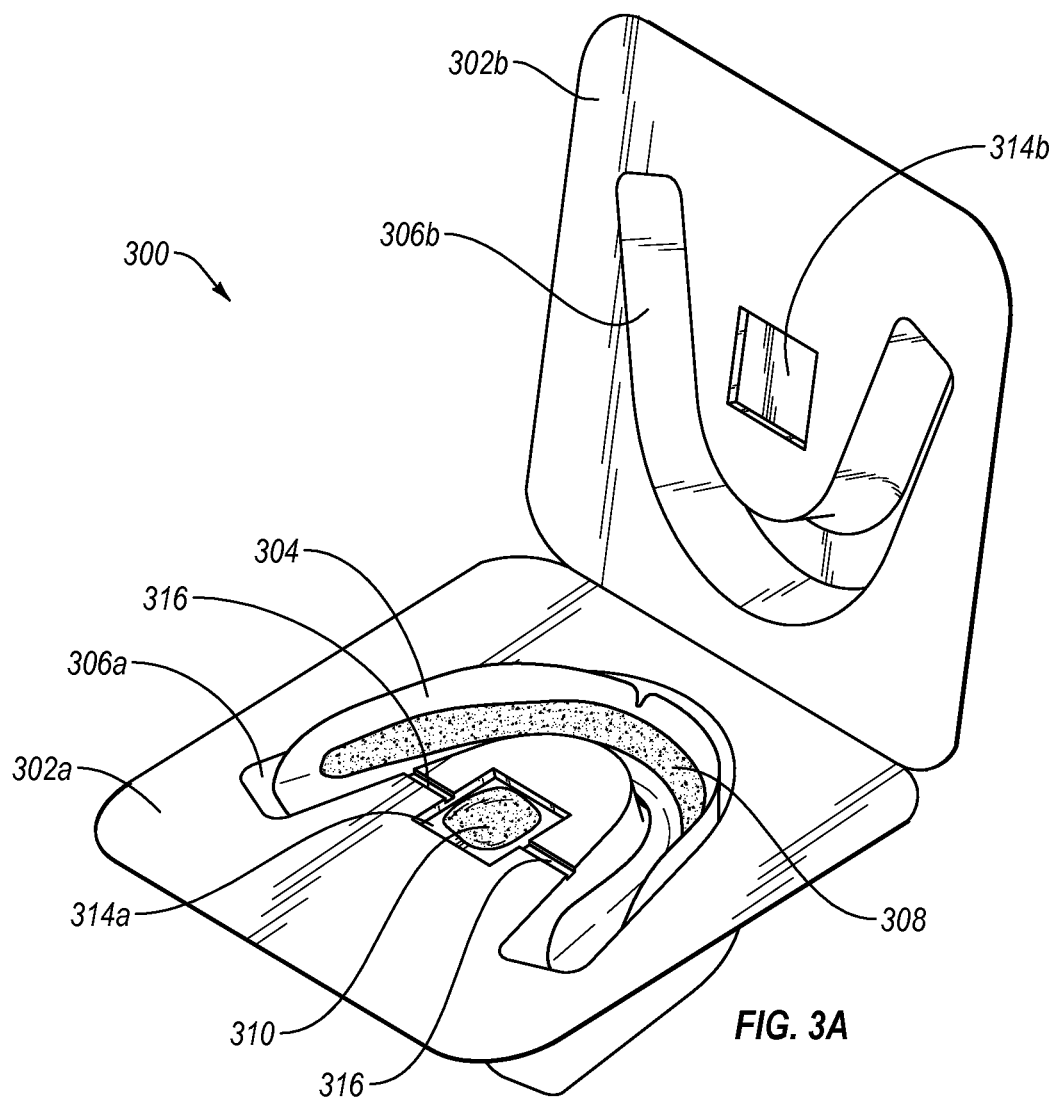
FIG. 3A schematically illustrates an exemplary packaging system having two halves which provide a reduced headspace so as to minimize the interior volume of the packaging system in which volatile components or gases may collect.
Figure 3B:
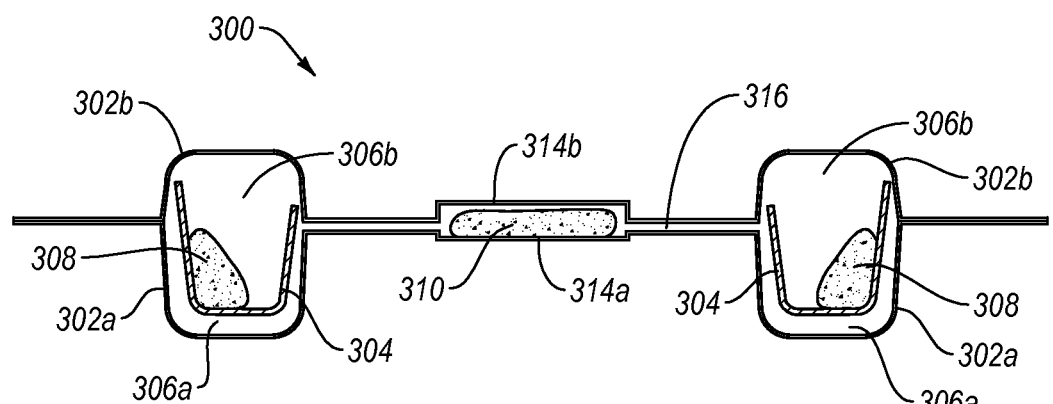
FIG. 3B is a cross-sectional view of the packaging system of FIG. 3A with the two halves in a sealed configuration to provide the reduced headspace.

FIGS. 3A and 3B illustrate an alternative packaging system 300 that further minimizes headspace, or the sealed interior volume, of packaging system 300 during storage in order to further preserve stability and potency of a composition stored therein. The packaging system 300 includes a first container half 302a and a second corresponding container half 302b which together form a sealed internal volume when their respective facial surfaces are sealed together.

An oral appliance (e.g., oral treatment tray) 304 may be positioned within a main well or compartment 306 defined by a first main compartment half 306a within the first container half 302a and a second main compartment half 306b within the second container half 302b. A main composition 308 is positioned within a trough of the oral treatment tray 304 and includes one or more volatile or gas-releasing components that may affect stability of the main composition 308.

A sacrificial composition 310 is positioned within an auxiliary well or compartment 314 defined by a first auxiliary compartment half 314a within the first container half 302a and a second auxiliary compartment half 314b within the second container half 302b. One or more channels 316 are provided in order to maintain fluid (e.g., gaseous) communication between the main compartment 306 and the auxiliary compartment 314 when the container halves 302a, 302b are joined together to form a sealed interior volume. The sacrificial composition 310 may include the same or similar volatile or gas-releasing component(s) as contained in the main composition 308, or may contain a different volatile or gas-releasing component having a greater vaporization rate that that of the main composition 3008, which may freely migrate from the auxiliary well or compartment 314 to the main well or compartment 306 to achieve equilibrium within the sealed interior volume of one or more vapors and/or gases released by main composition 308 into the headspace.

Figure 4A:
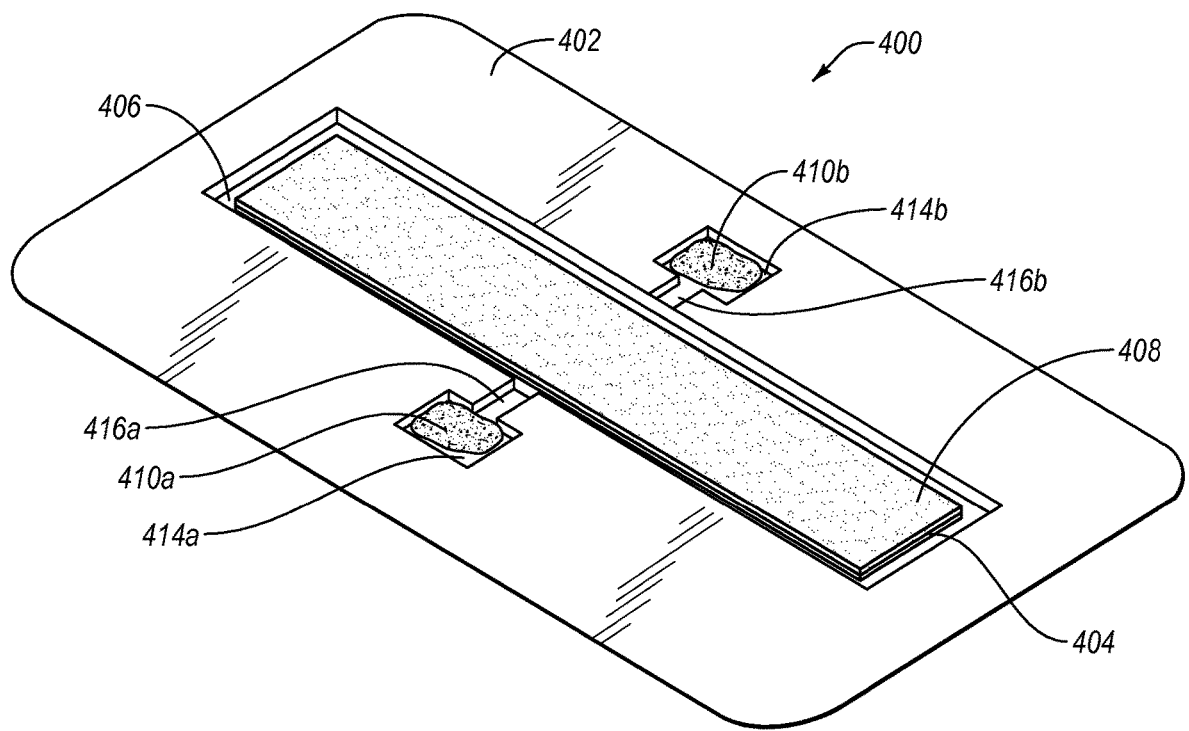
FIG. 4A schematically illustrates an alternative exemplary packaging container for use with a removable cover to form a packaging system for improving long-term stability of a flat treatment device, such as an oral treatment strip.
Figure 4B:
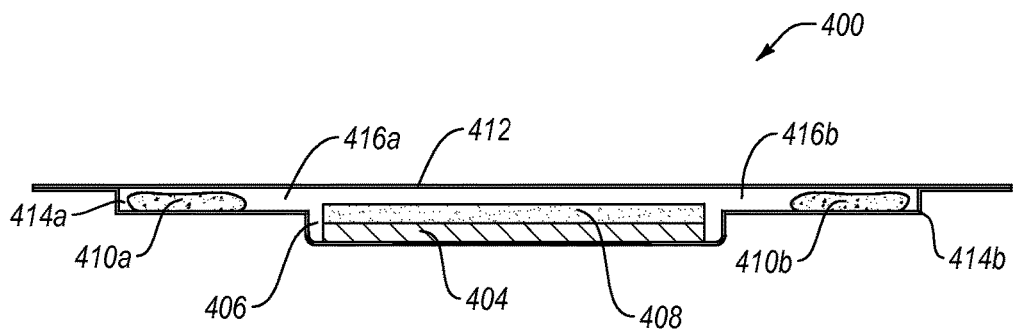
FIG. 4B is a cross-sectional view of the packaging container of FIG. 4A with a removable cover to form a packaging system for improving long-term stability of a flat treatment device, such as an oral treatment strip, stored within the packaging system.

FIGS. 4A and 4B illustrate an alternative packaging system 400 for use in storing an appliance that is substantially flat or of low profile. Packaging system 400 includes a packaging container 402 with a substantially flat appliance (e.g., strip-like barrier layer) 404 positioned within a shallow appliance well or compartment 406. A main composition (e.g., dental bleaching composition) 408 is positioned adjacent to appliance or barrier layer 404. A first sacrificial composition 410a is positioned within first auxiliary well or compartment 414a, which is in fluid (e.g., gaseous) communication with appliance well or compartment 406 by a first connecting channel 416a. A second sacrificial composition 410b is positioned within second auxiliary well or compartment 414b, which is in fluid (e.g., gaseous) communication with appliance well or compartment 406 by a second connecting channel 416b.

First and second sacrificial compositions 410a, 410b may be the same or different from each other and/or may be the same or different than the main composition 408. In the case where main composition 408 includes two or more stabilizing components, first and second sacrificial compositions 410a, 410b may contain different stabilizing components and/or different amounts of the stabilizing component(s).

As shown in FIG. 4B, the packaging system 400 further includes a removable cover 412, which may be formed from one or more materials that are substantially impervious to at least one of air, oxygen, moisture, or volatile materials, which forms a seal with the packaging container 402 when bonded or adhered thereto, and yields a sealed interior volume corresponding to the size of the appliance well or compartment 406. By way of example, removable cover 412 may include an opaque foil material. The packaging container 402 may itself be opaque, or it may be transparent or translucent. The sealed interior volume of the packaging system 400 maintains the main composition 408 and the sacrificial compositions 410a, 410b in fluid (e.g., gaseous) communication during storage so that the sacrificial compositions 410a, 410b may help maintain the stability and/or potency of the main composition 408 prior to use, thus increasing shelf-life of the main composition 408.

Figure 5A:
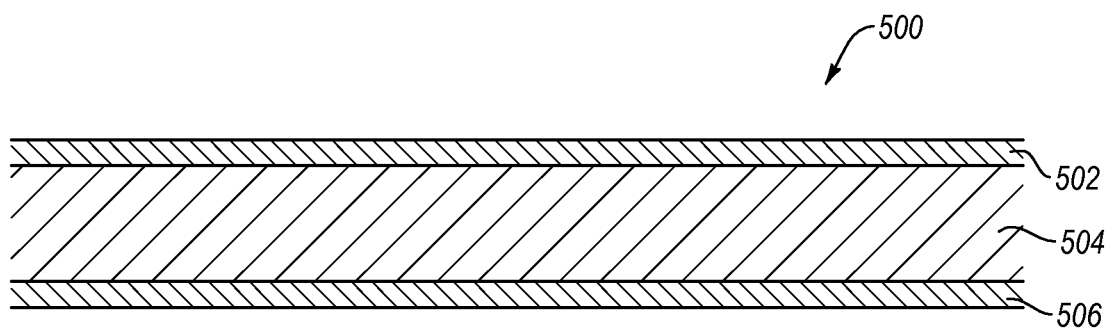
FIGS. 5A-5C illustrate exemplary laminate barrier materials for use in manufacturing packaging systems as disclosed herein.
Figure 5B:
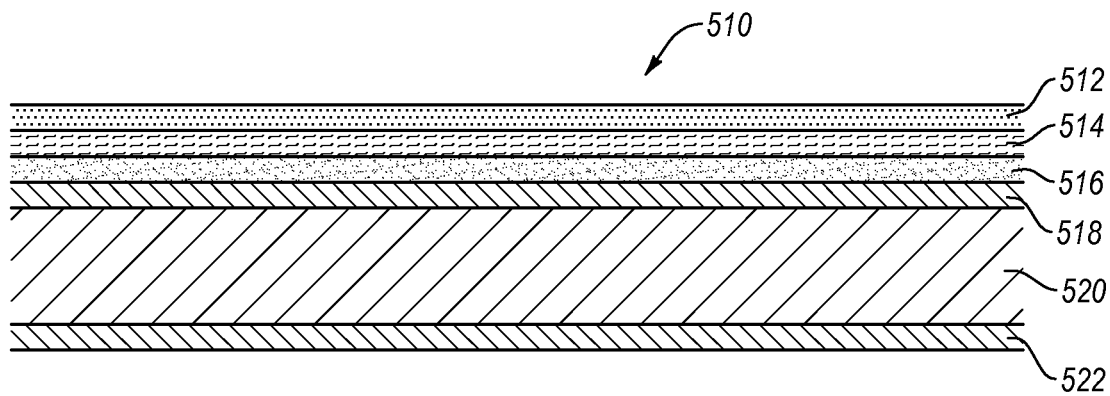
Figure 5C:
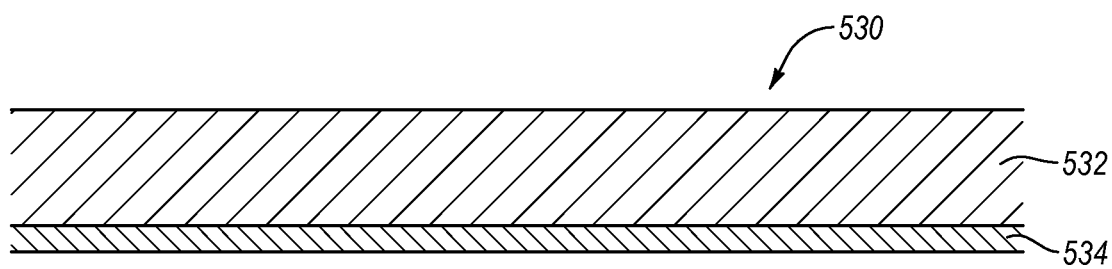

FIGS. 5A-5C illustrate various exemplary laminate structures that may be used in manufacturing packaging containers and packaging systems as disclosed herein. FIG. 5A is a cross sectional view illustrating an exemplary laminated polymer material 500. Laminated polymer material 500 is illustrated as including a first outer layer 502, a core layer 504, and a second outer layer 506. According to one embodiment, the core layer 504 may include a material having good water and/or oxygen molecule barrier properties (i.e., low permeability to water and/or oxygen molecules). The first and second outer layers 502, 506 may be formed of any suitable polymer material different from the core layer 504, and may be selected according to any desired property (e.g., good bondability to the core material 504, good oxygen and/or moisture barrier characteristics, good flow characteristics, low cost, and the like).

For example, the outer layers 502, 506 may be formed from polypropylene (PP) while the core layer 504 may be formed of COC. Polypropylene is easily bondable to COC, provides structure and bulk to the laminate polymer film, and is relatively inexpensive. Other materials for use in making the outer layers 502, 506 materials may include, but are not limited to, polyethylene (PE), polyvinylchloride (PVC), polyvinyldichloride (PVDC), or a glycol-modified polyethylene terephthalate (PETG). The outer layers 502, 506 and the core layer 504 may form a composite laminate material acts as a good barrier to water and oxygen molecules.

FIG. 5B is a cross sectional view illustrating another laminated polymer material, laminate 510. The laminate 510 is illustrated as including a total of six layers. In one example, a first three layers (512, 514, 516) may provide a first composite region that provides the laminate 510 with good oxygen barrier properties, while a second three layers (518, 520, 522) may provide a second composite region that provides the laminate 510 with good water vapor barrier properties. In way, that the laminate 510 may act as an effective barrier to both water vapor and oxygen gas (i.e., the laminate 510 is substantially impervious to both water and oxygen molecules). Some of the layers may be selected based on any desirable property (e.g., good bondability to an adjacent layer, good flow characteristics, or low cost).

By way of further example, layers 512 and 516 may comprise polyethylene, while layer 538 may comprise ethylene-vinyl alcohol (EVOH), which provides good oxygen barrier properties (i.e., is substantially impervious to oxygen molecules. The layers 512 and 516 are formed of polyethylene so as to bond well to EVOH layer 514 and provide bulk to that portion of the laminate 510. Layer 520 may be formed of COC to provide good water vapor barrier properties), while layers 518 and 522 may be formed of polypropylene, which has good bondability to COC layer 520. Polyethyelene layer 516 also exhibits good bondability to polypropylene layer 518. Although the described embodiment includes a COC layer encapsulated by PP and an EVOH layer encapsulated by PE, it is to be understood that the COC and EVOH layers may be encapsulated by any suitable materials (e.g., PP, PE, PVC, PVDC, similar materials, or combinations thereof). The layers may be co-extruded, using the heat of the extrusion process to bond the layers together, or the layers may be bonded together by use of suitable adhesives.

FIG. 5C is a cross sectional view illustrating another laminate polymer material 530 that includes two layers 532 and 534. In one such embodiment, first layer 532 may be formed of a material selected to provide good oxygen barrier properties, while second layer 534 may be formed of a material selected to provide good water molecule or vapor barrier properties. An example of such an embodiment includes a first layer 532 formed of BAREX, a nitrile copolymer available from BP Chemicals Inc., located in Naperville, Ill., and a second layer 534 formed of ACLAR, a PCTFE available from Honeywell Specialty Films in Morristown, N.J.

Example 1

A laminate polymer film suitable for thermoforming a packaging container having 6 layers, possessing good oxygen barrier properties, and being substantially impervious to water molecules is formed by co-extrusion. The compositions and thicknesses of the various layers are as follows:

| | | |
|---|---|---|
| $1^{st}$ Layer | PP | 1.5 mils |
| $2^{nd}$ Layer | COC | 12 mils |
| $3^{rd}$ Layer | PP | 1.5 mils |
| $4^{th}$ Layer | PE | 1.2 mils |
| $5^{th}$ Layer | EVOH | 0.4 mil |
| $6^{th}$ Layer | PE | 1.2 mils |

A packaging container having an appliance compartment and a sacrificial composition compartment or region is thermoformed from the laminate polymer film. An appliance and main composition are placed into the appliance compartment, a sacrificial composition is placed within the sacrificial composition compartment or region, and a peelable foil or other impermeable cover is adhered over the packaging container. The sealed packaging system acts as a substantially impervious barrier to water molecules, oxygen, air and volatile organic materials, allowing the main (e.g., dental treatment) composition sealed within the container to exhibit good stability, even when stored at room temperature for 24 months or more, particularly in view of the presence of the sacrificial composition.

Example 2

A laminate polymer film suitable for thermoforming a packaging container having 6 layers, possessing good oxygen barrier properties, and being substantially impervious to water molecules is formed by co-extrusion. The compositions and thicknesses of the various layers are as follows:

| | | |
|---|---|---|
| $1^{st}$ Layer | PP | 1.5 mils |
| $2^{nd}$ Layer | COC | 15 mils |
| $3^{rd}$ Layer | PP | 1.5 mils |
| $4^{th}$ Layer | PE | 1.2 mils |
| $5^{th}$ Layer | EVOH | 0.4 mil |
| $6^{th}$ Layer | PE | 1.2 mils |

A packaging container having an appliance compartment and a sacrificial composition compartment or region is thermoformed from the laminate polymer film. An appliance and main composition are placed into the appliance compartment, a sacrificial composition is placed within the sacrificial composition compartment or region, and a peelable foil or other impermeable cover is adhered over the packaging container. The sealed packaging system acts as a substantially impervious barrier to water molecules, oxygen, air and volatile organic materials, allowing the main (e.g., dental treatment) composition sealed within the container to exhibit good stability, even when stored at room temperature for 24 months or more, particularly in view of the presence of the sacrificial composition.

Example 3

A laminate polymer film suitable for thermoforming a packaging container having 6 layers, possessing good oxygen barrier properties, and being substantially impervious to water molecules is formed by co-extrusion. The compositions and thicknesses of the various layers are as follows:

| | | |
|---|---|---|
| $1^{st}$ Layer | PP | 1.5 mils |
| $2^{nd}$ Layer | COC | 18 mils |
| $3^{rd}$ Layer | PP | 1.5 mils |
| $4^{th}$ Layer | PE | 1.2 mils |
| $5^{th}$ Layer | EVOH | 0.4 mil |
| $6^{th}$ Layer | PE | 1.2 mils |

A packaging container having an appliance compartment and a sacrificial composition compartment or region is thermoformed from the laminate polymer film. An appliance and main composition are placed into the appliance compartment, a sacrificial composition is placed within the sacrificial composition compartment or region, and a peelable foil or other impermeable cover is adhered over the packaging container. The sealed packaging system acts as a substantially impervious barrier to water molecules, oxygen, air and volatile organic materials, allowing the main (e.g., dental treatment) composition sealed within the container to exhibit good stability, even when stored at room temperature for 24 months or more, particularly in view of the presence of the sacrificial composition.

Example 4

A laminate polymer film suitable for thermoforming a packaging container having 3 layers and being substantially impervious to water and volatile solvent or monomer molecules is formed by co-extrusion. The compositions and thicknesses of the various layers are as follows:

| | | |
|---|---|---|
| $1^{st}$ Layer | PP | 1.5 mils |
| $2^{nd}$ Layer | COC | 15 mils |
| $3^{rd}$ Layer | PP | 1.5 mils |

A packaging container having an appliance compartment and a sacrificial composition compartment or region is thermoformed from the laminate polymer film. An appliance and main composition are placed into the appliance compartment, a sacrificial composition is placed within the sacrificial composition compartment or region, and a peelable foil or other impermeable cover is adhered over the packaging container. The sealed packaging system acts as a substantially impervious barrier to water and volatile solvent or monomer molecules, allowing the main (e.g., dental adhesive) composition sealed within the container to exhibit good stability, even when stored at room temperature for 24 months or more, particularly in view of the presence of the sacrificial composition.

Example 5

A laminate polymer film suitable for thermoforming a packaging container having 3 layers and being substantially impervious to water and volatile solvent or monomer molecules is formed by co-extrusion. The compositions and thicknesses of the various layers are as follows:

| | | |
|---|---|---|
| $1^{st}$ Layer | PP | 1.5 mils |
| $2^{nd}$ Layer | COC | 18 mils |
| $3^{rd}$ Layer | PP | 1.5 mils |

A packaging container having an appliance compartment and a sacrificial composition compartment or region is thermoformed from the laminate polymer film. An appliance and main composition are placed into the appliance compartment, a sacrificial composition is placed within the sacrificial composition compartment or region, and a peelable foil or other impermeable cover is adhered over the packaging container. The sealed packaging system acts as a substantially impervious barrier to water and volatile solvent or monomer molecules, allowing the main (e.g., dental adhesive) composition sealed within the container to exhibit good stability, even when stored at room temperature for 24 months or more, particularly in view of the presence of the sacrificial composition.

Example 6

A laminate polymer film suitable for thermoforming a packaging container having 7 layers, possessing good oxygen barrier properties, and being substantially impervious to water molecules is formed by co-extrusion. The compositions and thicknesses of the various layers are as follows:

| | | |
|---|---|---|
| $1^{st}$ Layer | PP | 1.5 mils |
| $2^{nd}$ Layer | COC | 12 mils |
| $3^{rd}$ Layer | PP | 1.5 mils |
| $4^{th}$ Layer | PE | 1.2 mils |
| $5^{th}$ Layer | EVOH | 0.4 mil |
| $6^{th}$ Layer | PE | 1.2 mils |
| $7^{th}$ Layer | ACLAR | 2 mils |

A packaging container having an appliance compartment and a sacrificial composition compartment or region is thermoformed from the laminate polymer film. An appliance and main composition are placed into the appliance compartment, a sacrificial composition is placed within the sacrificial composition compartment or region, and a peelable foil or other impermeable cover is adhered over the packaging container. The sealed packaging system acts as a substantially impervious barrier to water molecules, oxygen, air, and volatile organic materials, allowing the main (e.g., dental treatment) composition sealed within the container to exhibit good stability, even when stored at room temperature for 24 months or more, particularly in view of the presence of the sacrificial composition.

Example 7

A laminate polymer film suitable for thermoforming a packaging container having only 2 layers, possessing good oxygen barrier properties, and being substantially impervious to water molecules is formed by co-extrusion. The compositions and thicknesses of the various layers are as follows:

| | | |
|---|---|---|
| $1^{st}$ Layer | ACLAR | 3 mils |
| $2^{nd}$ Layer | BAREX | 14 mils |

A packaging container having an appliance compartment and a sacrificial composition compartment or region is thermoformed from the laminate polymer film. An appliance and main composition are placed into the appliance compartment, a sacrificial composition is placed within the sacrificial composition compartment or region, and a peelable foil or other impermeable cover is adhered over the packaging container. The sealed packaging system acts as a substantially impervious barrier to both water molecules and oxygen, allowing the main (e.g., dental treatment) composition sealed within the container to exhibit good stability, even when stored at room temperature for 24 months or more, particularly in view of the presence of the sacrificial composition.

Example 8

A laminate polymer film suitable for thermoforming a packaging container having 3 layers and being substantially impervious to water molecules is cold formed. The layer compositions and thicknesses are initially as follows:

| | | |
|---|---|---|
| $1^{st}$ Layer | PP | 1.5 mils |
| $2^{nd}$ Layer | COC | 15 mils |
| $3^{rd}$ Layer | PP | 1.5 mils |

A packaging container having an appliance compartment and a sacrificial composition compartment or region is thermoformed from the laminate polymer film. An appliance and main composition are placed into the appliance compartment, a sacrificial composition is placed within the sacrificial composition compartment or region, and a peelable foil or other impermeable cover is adhered over the packaging container. The sealed packaging system acts as a substantially impervious barrier to water and volatile solvent or monomer molecules, allowing the main (e.g., dental adhesive) composition sealed within the container to exhibit good stability, even when stored at room temperature for 24 months or more, particularly in view of the presence of the sacrificial composition.

Example 9

A laminate polymer film suitable for thermoforming a packaging container having 6 layers, possessing good oxygen barrier properties, and being substantially impervious to water molecules is formed. The compositions and thicknesses of the various layers are as follows:

| | | |
|---|---|---|
| $1^{st}$ Layer | PP | 1.5 mils |
| $2^{nd}$ Layer | COC | 12 mils |
| $3^{rd}$ Layer | PP | 1.5 mils |
| $4^{th}$ Layer | PE | 1.2 mils |
| $5^{th}$ Layer | EVOH | 0.4 mil |
| $6^{th}$ Layer | PE | 1.2 mils |

A packaging container having an appliance compartment and a sacrificial composition compartment or region is thermoformed from the laminate polymer film. An appliance and main composition are placed into the appliance compartment, a sacrificial composition is placed within the sacrificial composition compartment or region, and a peelable foil or other impermeable cover is adhered over the packaging container. The sealed packaging system acts as a substantially impervious barrier to water molecules, oxygen, air, and volatile organic materials, allowing the main (e.g., dental treatment) composition sealed within the container to exhibit good stability, even when stored at room temperature for 24 months or more, particularly in view of the presence of the sacrificial composition.

Example 10

A laminate polymer film suitable for thermoforming a packaging container is manufactured by re-arranging any of the polymer layers of Examples 1-9.

Example 11

A laminate polymer film suitable for cold forming a packaging container is manufactured by substituting a polymer layer of Examples 1-10 with a metal foil layer.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A packaging system, comprising:
    a container and a removable cover defining a sealed container having a sealed interior volume, the container including:
        an appliance well or compartment configured to contain a dental appliance and a dental composition; and
        an auxiliary well or compartment separate from and in fluid communication with the appliance well or compartment and configured to contain a sacrificial composition; and
    the dental appliance and the dental composition being positioned within the appliance well or compartment, the dental composition including at least one volatile material or gas-releasing component; and
    the sacrificial composition being positioned within the auxiliary well or compartment, the sacrificial composition including a stabilizing component that replaces the at least one volatile material or gas-releasing material within the dental composition or displaces the at least one volatile material or gas-releasing material within the sealed interior volume of the sealed container.

2. A packaging system as in claim 1, wherein the sealed container is substantially impervious to the at least one volatile material or gas-releasing material.

3. A packaging system as in claim 1, wherein the container comprises a laminate structure including at least one barrier layer substantially impervious to at least one of air, oxygen, other gases, moisture, or volatile material and at least one structural layer that provides strength and rigidity to the laminate structure.

4. A packaging system as in claim 3, wherein the laminate structure comprises at least one barrier material substantially impervious to oxygen molecules selected from the group of ethylene-vinyl alcohol copolymer (EVOH), propylene-vinyl alcohol copolymer (PVOH), polyvinylidene chloride (PVDC), polyamides, nylons, nitrile copolymers, polyacrylonitriles (PAN), polyethylene terephthalate (PET), resorcinol, ormocers, liquid crystal polymers (LCPs), aliphatic polyketones, plasma glass coatings, thermoset epoxy coatings, and nanocomposites.

5. A packaging system as in claim 3, wherein the laminate structure comprises at least one barrier material substantially impervious to water molecules selected from the group of cyclic olefin polymers (COPs), cyclic olefin copolymers (COCs), polychlorotrifluoroethylene (PCTFE), aluminum oxide coatings (AlOx), vinylidene chloride copolymers, high density polyethylene (HDPE), and polypropylene.

6. A packaging system as in claim 3, wherein the laminate structure comprises at least one structural polymer selected from the group of polyolefins, polyesters, polypropylene (PP), polyethylene (PE), polyvinylchloride (PVC), polyvinyldichloride (PVDC), ethylene-vinyl acetate copolymer (EVA), and glycol-modified polyethylene terephthalate (PETG).

7. A packaging system as in claim 1, wherein the removable cover comprises at least one of foil, paper, or laminate material.

8. A packaging system as in claim 1, wherein the appliance well or compartment has a shape that corresponds to a shape of the dental appliance.

9. A packaging system as in claim 1, further comprising a passageway between the appliance well or compartment and the auxiliary well or compartment.

10. A packaging system as in claim 9, wherein the sealed interior volume is less than about 500%, of a cumulative volume of the dental composition and the sacrificial composition.

11. A packaging system as in claim 1, wherein the dental appliance comprises a dental treatment tray.

12. A packaging system as in claim 1, wherein the at least one gas-releasing material in the dental composition comprises a peroxide, and wherein the stabilizing component in the sacrificial composition emits oxygen.

13. A packaging system as in claim 1, wherein the at least one volatile material is selected from the group consisting of water and organic solvents.

14. A packaging system as in claim 1, wherein the dental composition is an adhesive composition including at least one of a volatile solvent or volatile monomer, wherein the stabilizing component of the sacrificial composition comprises the volatile solvent or volatile monomer.

15. A packaging system as in claim 1, wherein the sacrificial composition has the same composition as the dental composition.

16. A packaging system as in claim 1, wherein the stabilizing component of the sacrificial composition comprises the at least one volatile material or gas-releasing material of the dental composition.

17. A packaging system as in claim 16, wherein the sacrificial composition comprise a greater concentration or amount of the at least one volatile material or gas-releasing material than the dental composition.

18. A packaging system as in claim 1, wherein the at least one stabilizing component of the sacrificial composition has a vaporization rate greater than or equal to a vaporization rate of the at least one volatile material or gas-releasing material of the dental composition.

19. A packaging system, comprising:
a container and a removable cover defining a sealed container having a sealed interior volume, the container including an appliance well or compartment configured to contain a dental appliance and a dental composition and an auxiliary well or compartment separate from and in fluid communication with the appliance well or compartment and configured to contain a sacrificial composition;
the dental composition being positioned in the appliance well or compartment and comprising at least one volatile material or gas-releasing material; and
the sacrificial composition being positioned in the auxiliary well or compartment and including a stabilizing component that replaces the at least one volatile material or gas-releasing component within the dental composition or displaces the at least one volatile material or gas-releasing material within the sealed interior volume of the sealed container.

20. A packaging system as in claim 19, wherein the dental composition is a dental treatment composition or a dental adhesive composition.

21. A packaging system as in claim 19, further comprising a dental treatment tray in the appliance well or compartment and having the dental composition disposed thereon, and wherein the dental composition comprises a dental bleaching composition comprising a peroxide.

22. A packaging system as in claim 19, wherein the fluid communication is established by at least one passageway between the appliance well or compartment and the auxiliary well or compartment.

23. A packaging system as in claim 19, wherein the container comprises a laminate structure including at least one barrier layer substantially impervious to at least one of air, gases, moisture, or volatile material and at least one structural layer that provides strength and rigidity to the laminate structure, and wherein at least one of the container and the removable cover is substantially impervious to at least one of air, gases, moisture, or volatile material.

24. A packaging system, comprising:
a container and removable cover defining a sealed container having a sealed interior volume, the container including an appliance well or compartment configured to contain a dental bleaching device and an auxiliary well or compartment separate from and in fluid communication with the appliance well or compartment and configured to contain a sacrificial composition;
the dental bleaching device being disposed within the appliance well or compartment and comprising:
a barrier layer configured for placement over at least a portion of a person's teeth; and
a dental bleaching composition disposed adjacent to the barrier layer and comprising a peroxide that releases oxygen upon decomposition; and
the sacrificial composition being disposed in the auxiliary well or compartment and containing an oxygen-releasing material which emits oxygen within the sealed interior volume of the sealed container and reduces decomposition of the peroxide prior to removing the removable cover,
wherein the container and removable cover each comprise at least one material that is substantially impervious to at least one of oxygen or water vapor.

25. A packaging system as in claim 24, wherein the dental bleaching composition comprises water, and wherein the sacrificial composition comprises water that forms water vapor within the sealable interior volume and reduces evaporation of water from the dental bleaching composition prior to removing the removable cover.

26. A packaging system as in claim 24, wherein the dental bleaching composition has an initial concentration of peroxide when initially placed within the sealed interior volume, wherein the packaging system maintains at least about 85% of the initial concentration of peroxide after at least 3 months.

* * * * *

UNITED STATES PATENT AND TRADEMARK OFFICE
CERTIFICATE OF CORRECTION

| | |
|---|---|
| PATENT NO. | : 10,874,495 B2 |
| APPLICATION NO. | : 15/122333 |
| DATED | : December 29, 2020 |
| INVENTOR(S) | : Allred et al. |

Page 1 of 2

It is certified that error appears in the above-identified patent and that said Letters Patent is hereby corrected as shown below:

In the Specification

Column 2
Line 30, change "According one" to –According to one–
Line 34, change "According one" to –According to one–

Column 3
Line 36, delete second instance of "or"
Line 53, change "configured to similar" to –configured to be similar–
Line 54, change "molecules in as a" to –molecules in a–
Line 55, change "molecules the" to –molecules in the–

Column 5
Line 43, change "properties, as" to –properties, such as–

Column 9
Line 66, change "headspace to respect" to –headspace with respect–

Column 10
Line 5, delete "an" and change "are" to –is–
Line 23, change "gas a" to –gas as a–
Line 56, change "gas a" to –gas as a–

Column 12
Line 40, change "gas a" to –gas as a–
Line 55, delete "in"

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*

Column 13
Line 25, change "gas a" to –gas as a–
Line 27, change "2210b" to –210b–
Line 55, change "enclosed" to –enclose–

Column 14
Line 24, change "3008" to –308–

Column 15
Line 29, change "material acts" to –material that acts–
Line 39, change "In way, that" to –In that way,–
Line 46, change "538" to –514–

In the Claims

Column 21
Line 51, change "comprise" to –comprises–